United States Patent [19]

Arai et al.

[11] Patent Number: 5,406,609
[45] Date of Patent: Apr. 11, 1995

[54] X-RAY ANALYSIS APPARATUS

[75] Inventors: Tomoya Arai; Takashi Shoji, both of Takatsuki, Japan

[73] Assignee: Rigaku Industrial Corporation, Osaka, Japan

[21] Appl. No.: 44,508

[22] Filed: Apr. 9, 1993

[30] Foreign Application Priority Data

| Apr. 9, 1992 | [JP] | Japan | 4-117934 |
| Sep. 24, 1992 | [JP] | Japan | 4-280964 |

[51] Int. Cl.$^6$ .................................. G21K 1/06
[52] U.S. Cl. ........................ 378/73; 378/45; 378/84; 378/83
[58] Field of Search .............. 378/73, 82–85, 378/45

[56] References Cited

U.S. PATENT DOCUMENTS 4,916,721  4/1990  Carr et al. .................... 378/82

FOREIGN PATENT DOCUMENTS 4169898  6/1992  Japan .

OTHER PUBLICATIONS

"New method for focusing x rays and gamma rays" R. K. Smither, Rev. Sci. Instrum. 53(2), Feb. 1982, pp. 131–141.

*Primary Examiner*—Craig E. Church

[57] ABSTRACT

An X-ray analysis apparatus including an artificial multi-layered grating for rendering X-ray beams to be monochromatic before they are incident on a specimen to be analyzed. This artificial multi-layered grating operates to diffract the X-ray beam, generated from an X-ray radiation source and subsequently impinging on a reflective surface of the artificial multi-layered grating, at a predetermined angle of diffraction to provide the monochromatic X-ray beams. The periodicity of the spacing of lattice planes of the artificial multi-layered grating is so chosen as to be of a value progressively varying along the reflective surface thereof with an increase in distance from the X-ray radiation source. The X-ray analysis apparatus herein disclosed is designed to avoid any possible reduction of the intensity of the X-ray beams which would occur when they are rendered to be monochromatic, and to increase the intensity of the X-ray beams to ensure an improved accuracy in spectroscopic analysis.

14 Claims, 11 Drawing Sheets

Fig. 6(a)
Fig. 6(b)
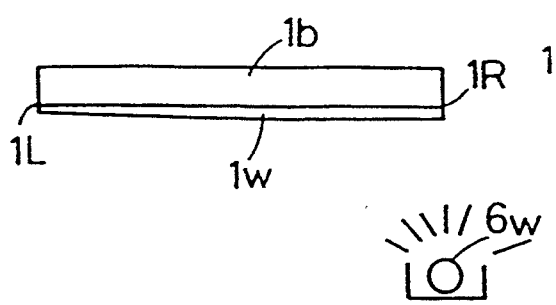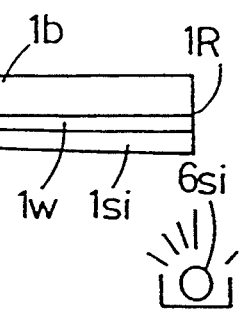
Fig. 6(c)
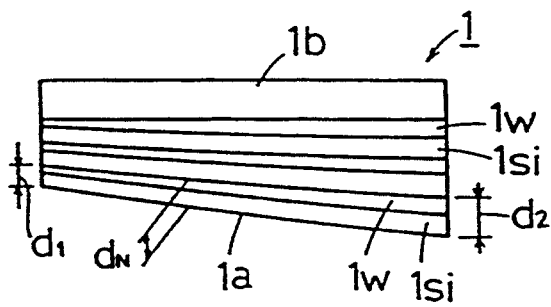
Fig. 7
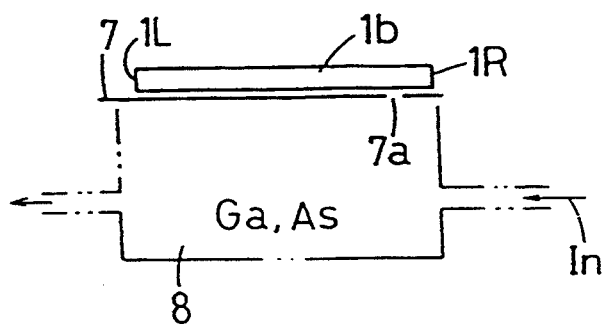

X-RAY ANALYSIS APPARATUS

BACKGROUND OF THE INVENTION

1. Field of the Invention

The present invention generally relates to an X-ray analysis apparatus for analyzing specimens by irradiating X-rays and, more particularly, to the X-ray analysis apparatus of a type utilizing an artificial multi-layered grating.

2. Description of the Prior Art

The X-ray analysis is currently carried out by using either an X-ray diffraction technique or a fluorescent X-ray technique. In the practice of the X-ray diffraction analysis, substantially collimated X-ray are irradiated to a specimen to be analyzed while the specimen is rotated in one direction, and the X-rays diffracted from the specimen are then detected for calculation according to Bragg's law to determine the spacing of lattice planes thereby to analyze the crystal structure of the specimen. On the other hand, X-ray fluorescence analysis is to measure the fluorescent X-rays which are emitted from a specimen by means of irradiation of primary X-rays generated from an X-ray tube.

The total reflection fluorescent X-ray analysis, which is a kind of the X-ray fluorescence analysis techniques, is carried out by irradiating the specimen with a first-order X-ray so as to be incident on a surface of the specimen at an incident angle so small as to result in a total reflection of the X-ray beams and then detecting fluorescent X-rays generating from the specimen for the determination of elements comprising the specimen. The Japanese Laid-open Patent Publication No. 63-78056 published in 1988, for example, discloses the utilization of this total reflection fluorescent X-ray analysis for the detection of impurities sticking to a surface of the specimen.

In the practice of any one of these X-ray analysis methods, in order to reduce an error in analytical measurement, a curved analyzing element is utilized to provide monochromatic X-rays for irradiation to the specimen to be analyzed. It has, however, been found that, when the source X-rays are passed through the analyzing crystal to provide the monochromatic X-rays, the intensity of the X-rays tends to be lowered to such an extent that no reduction of the analytical error be longer obtained. This will be discussed in more detail for each case with the X-ray diffraction analysis and the total reflection fluorescent X-ray analysis.

FIG. 11 illustrates schematically the prior art X-ray diffraction analysis apparatus.

Referring now to FIG. 11, reference numeral 50 represents an analyzing crystal or a monochromator. This analyzing crystal 50 has a reflective surface 51 used to diffract X-ray beams B1 generating from an X-ray radiation source P, to provide first monochromatic X-ray beams B2 which are subsequently incident on a specimen 2. The first monochromatic X-ray beams are, after having been once converged at an X-ray collecting point Q, diverged again before they impinge upon the specimen 2. A X-ray detector 3 is utilized to detect second monochromatic X-ray beams B6 which have been reflected from the specimen 2. The specimen 2 and the X-ray detector 3 are during the measurement rotated at an angular velocity ratio of 1:2, and the angle of diffraction of the second monochromatic X-ray beams B6 and the wavelength thereof, both detected by the X-ray detector, provide an indication of the crystal structure of the specimen 2.

While it has been recognized that the composition of the specimen 2 more or less varies with a change in position of site of analysis, the above discussed prior art X-ray diffraction analysis has made it possible to analyze the specimen over a relatively large surface area, for example, 1 to 2 square centimeter.

However, since the first diffracted X-ray beams B2 diverge after having been converged at the X-ray collecting point Q, the X-ray path length inevitably becomes long. At the same time, the first diffracted X-ray beams B2 having been diverged travel not only in a direction parallel to the sheet of the drawing of FIG. 11, but also in a direction Z perpendicular to the sheet of the drawing of FIG. 11. Because of these reasons, the intensity of the X-ray beams eventually detected by the X-ray detector 3 tends to be lowered, resulting in a less accurate analytical measurement.

In any event, in this prior art optical system, the divergent angle $\Omega o$ of the diverging X-ray beams B1 generating from the X-ray radiation source P and subsequently impinging upon the curved analyzing crystal 50 is equal to the convergent angle $\Omega$ at which the first diffracted monochromatic X-ray beams B2 are converged at the X-ray collecting point Q. Because of this, in the case of the X-ray diffraction analysis wherein the first diffracted monochromatic X-ray beams B2 are required to be converged substantially parallel at a small convergent angle $\Omega$ before a specimen (not shown) is irradiated, the divergent angle $\Omega o$ of the X-ray beams B1 generating from the X-ray radiation source P must be small. Accordingly, since the intensity of the X-ray beams B1 impinging upon the analyzing crystal 50 decreases in proportion to the reduction of the divergent angle $\Omega o$ determined by the dimensions of the reflective surface 51, the intensity of the first diffracted monochromatic X-ray beams B2 ready to be incident upon the specimen tends to be lowered and, therefore, no reduction can be expected of the analytical error.

FIG. 12 illustrates the prior art total reflection fluorescence X-ray analysis apparatus. In this apparatus, X-ray beams B1 generating from the X-ray radiation source (X-ray source) P of an X-ray tube 5, travel towards a well-known Johanson monochromator crystal (analyzing crystal) 1A through a slit 5a. Characteristic X-ray beams of a predetermined wavelength contained in the X-ray beams B1 are diffracted by the monochromator crystal 1A to provide monochromatic X-ray beams (first-order X-ray beams) B2 which are subsequently impinge upon a surface 2a of the specimen 2 at a small incident angle $\alpha$, for example, 0.05 to 0.20 degree. A portion of the diffracted monochromatic X-ray beams B2 incident upon the specimen 2 undergoes a total reflection to provide reflected X-ray beams B4 while the remaining diffracted monochromatic X-ray beams B2 excite the specimen 2 to cause the latter to emit fluorescent X-ray beams B5 peculiar to analyzing elements contained in the specimen 2. The fluorescent X-ray beams B5 emitted from the specimen 2 are subsequently detected by an X-ray detector 3, disposed in face-to-face relationship with the surface 2a of the specimen 2. The X-ray detector 3 then determines the intensity of the fluorescent X-ray beams B5 and provides a detection signal a which is subsequently fed to a multi-pulse-height analyzer for providing X-ray spectra of interest.

In the above described total reflection fluorescence X-ray analysis, since the incident angle α of the diffracted monochromatic X-ray beams (first-order X-ray beams) B2 is very small, there is such an advantage that no substantial quantity of the totally reflected X-ray beams B4 as well as scattered X-ray beams enter the X-ray detector 4 and, therefore, as compared with an output level of the fluorescent X-ray beams B5 detected by the X-ray detector 3, a noise component is very small enough to provide a high signal-to-noise ratio (S/N ratio). For this reason, the sensitivity of analysis is so high as to make it available for the determination of a extremely small amount of impurities. In view of this, the total reflection fluorescence X-ray analysis is effectively and largely utilized for analyzing a surface contamination of silicon wafers.

In the practice of the prior art total reflection fluorescence X-ray analysis, since the analyzing crystal 1A is utilized to provide the primary monochromatic X-ray beams B2, the intensity of the scattering X-ray beams can be minimized to reduce the analytical error. On the other hand, however, if the X-ray beams B1 are rendered to be monochromatic, the intensity of the diffracted X-ray beams B2 is considerably lowered. This lowering of the intensity of the diffracted X-ray beams B2 is eliminated by the use of the curved analyzing crystal 1A so that the diffracted monochromatic X-ray beams B2 ace collected on the surface 2a of the specimen 2 to compensate for a reduction in intensity of the diffracted monochromatic X-ray beams B2 used to excite the specimen 2.

Unlike the standard fluorescence X-ray analysis apparatus, the prior art total reflection fluorescence X-ray analysis apparatus is ineffective to sufficiently increase the intensity of the diffracted monochromatic X-ray beams B2 used to irradiate the specimen even though the curved analyzing crystal 1A is employed. The reason therefor will now be discussed.

In this type of optical system, the divergent angle $\Omega_o$ of the diverging X-ray beams B1 generated from the X-ray radiation source P and subsequently impinging upon the analyzing crystal 1A is equal to the convergent angle $\Omega$ at which the diffracted X-ray beams B2 are converged. On the other hand, in the total reflection fluorescence X-ray analysis, the incident angle α of the diffracted X-ray beams B2 upon the surface 2a of the specimen 2 is required to be small of 0.05 to 0.20 degree as hereinbefore described and, therefore, the divergent angle $\Omega_o$ of the X-ray beams B2 diffracted from the analyzing crystal 1A must be chosen to be about 0.1 degree. This means that the divergent angle $\Omega_o$ of the X-ray beams B1 before they are rendered to be monochromatic must be reduced to a very small value. Accordingly, the intensity of the diffracted monochromatic X-ray beams B2 ready to be incident upon the specimen tends to be lowered and, therefore, no satisfactory and sufficient reduction can be expected of the analytical error.

SUMMARY OF THE INVENTION

The present invention has been devised to minimize or substantially eliminate the foregoing problems discussed in connection with the prior art X-ray diffraction analysis apparatus and is intended to provide an improved X-ray diffraction analysis apparatus utilizing the curved analyzing element to provide monochromatic beams, wherein the intensity of the X-ray beams incident upon the X-ray detector system is increased to reduce the X-ray analytical error.

The X-ray diffraction analysis apparatus according to one aspect of the present invention comprises an artificial multi-layered grating having a reflective surface of a predetermined profile having a periodicity of the spacing of lattice planes progressively increasing as a position on the artificial multi-layered grating goes away from an X-ray radiation source such that an X-ray beam emitted from the X-ray radiation source is diffracted to provide a monochromatic diffracted X-ray beam. This artificial multi-layered grating is usable to cause the monochromatic diffracted X-ray beam to be incident on the specimen with a reduced divergent angle while the monochromatic diffracted X-ray beam is allowed to diverge. The apparatus also comprises an X-ray detector for receiving a second diffracted X-ray beam diffracted by the specimen, and a goniometer for rotating the specimen and the X-ray detector at an angular velocity ratio of 1:2 relative to each other.

According to the above described aspect of the present invention, if the periodicity d increases, that is, at a point of reflection at the X-ray analyzing element which is furthest from the X-ray radiation source, the reflection angle increases such that the virtual convergent angle (divergent angle), at which the monochromatic diffracted X-ray beam converges can be reduced to a value smaller than the divergent angle. Accordingly, the X-ray beam emitted from the X-ray radiation source at a relatively great divergent angle towards the artificial multi-layered grating can impinge upon the specimen with a relatively small virtual convergent angle (divergent angle) and, therefore, the decrease of the intensity of the diffracted X-ray beam can be suppressed to increase the intensity as compared with that afforded by the prior art X-ray diffraction analysis apparatus.

The total reflection fluorescent X-ray analysis apparatus according to another aspect of the present invention comprises an X-ray radiation source for emitting an X-ray beam, and an analyzing element in the form of an artificial multi-layered grating for diffracting the X-ray beam from the X-ray radiation source to provide a first-order monochromatic diffracted X-ray beam which is converged on a surface of the specimen at a small incident angle sufficient to cause the X-ray beam to undergo a total reflection. This artificial multi-layered grating has a reflective surface of a predetermined profile having a periodicity of the spacing of lattice planes progressively increasing as a position on the artificial multi-layered grating goes away from the X-ray radiation source. The apparatus also comprises an X-ray detector for detecting a fluorescent X-ray beam emitted from the specimen as the specimen is excited by the first-order monochromatic diffracted X-ray beam and for analyzing the detected fluorescent X-ray beam based on a result of detection by said X-ray detector.

According to the above described aspect of the present invention, if the periodicity increases, that is, at a point of reflection at the X-ray analyzing element which is furthest from the X-ray radiation source, the reflection angle increases such that the convergent angle of the first-order monochromatic diffracted X-ray beam becomes smaller than the divergent angle of the X-ray generated from the X-ray radiation source. Accordingly, the radiant X-ray beam generated from the X-ray radiation source at a relatively great divergent angle towards the artificial multi-layered grating can impinge upon the specimen at a relatively small convergent angle (divergent angle) and, therefore, the decrease of the intensity of the diffracted X-ray beam can be suppressed to increase the intensity as compared with that afforded by the prior art X-ray diffraction analysis apparatus. Consequently, the error of the analytical measurement can advantageously be reduced.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIGS. 6(a) to 6(c) illustrate the sequence of a method of making the artificial multi-layered grating at respective process steps, respectively;

FIG. 7 illustrates another method of making the artificial multi-layered grating;

DETAILED DESCRIPTION OF THE INVENTION

The basic structure and the principle of operation of the X-ray diffraction analysis apparatus configured to accomplish the foregoing object of the present invention will be discussed with reference to FIG. 1 which illustrates a first preferred embodiment of the present invention.

Figure 1:
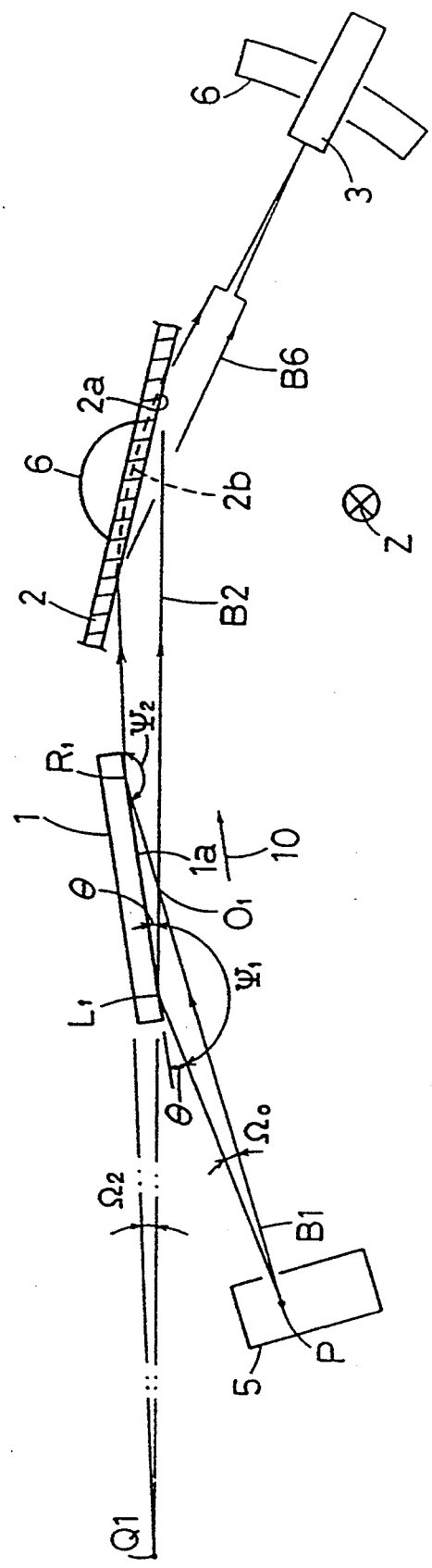
FIG. 1 is a schematic diagram showing an X-ray diffraction analysis apparatus according to a first preferred embodiment of the present invention.

The present invention makes use of an artificial multi-layered grating identified by 1 in FIG. 1. As shown therein, the artificial multi-layered grating 1 has a reflective surface 1a operable to diffract an X-ray beam B1 irradiated from the X-ray radiation source P and subsequently impinging upon the grating surface 1a at an incident angle $\theta$, thereby to provide a monochromatic X-ray beam. This artificial multi-layered grating 1 is so designed and so configured that the periodicity d of the spacing of the lattice planes progressively increases along the grating surface 1a wherefor, when in use with the X-ray beam B1 impinging thereon, the first diffracted monochromatic X-ray beam B2 is caused to be incident upon the specimen 2, while being diverged, but at a divergent angle $\Omega_o$ reduced to a value about equal to the virtual convergent angle (divergent angle) $\Omega_2$. So far associated with the X-ray radiation source P, the periodicity d is chosen to have a value progressively increasing as the artificial multi-layered grating 1 goes away from the X-ray radiation source P as shown by the arrow 10. The first diffracted monochromatic X-ray beam B2 is diffracted by a virtual curved surface 2b in the specimen 2 to provide a second diffracted X-ray beam B6 which is subsequently detected by an X-ray detector 3. The specimen 2 and the X-ray detector 3 are rotated at an angular velocity ratio of 1:2 by a goniometer.

The X-ray diffraction analysis of the specimen 2 is based on the angle of diffraction of and the wavelength of the second diffracted X-ray beam B6 to determine the spacing of the lattice plane of a substance contained in the specimen 2.

The basic condition of X-ray diffraction is given by a well-known Bragg's equation:

$$2d \cdot \sin \theta = n\lambda$$

wherein $\theta$ represents the incident angle or the angle of diffraction, $\lambda$ represents the wavelength of the X-ray beam, and n represents the number of the order of reflection.

If the reflection angle between the incident X-ray beam B1 and the diffracted X-ray beam B2 is expressed by $\Psi_N$ (wherein N represents a positive integer as actually employed in FIG. 1), the Bragg's equation can be rewritten as follows:

$$2d \cdot \sin \theta \{(\pi - \Psi_N)/2\} = n\lambda \quad (1)$$

In FIG. 1, $\Psi_1$ and $\Psi_2$ are shown as representative values. The equation (1) above can be modified as follows:

$$2d \cdot \cos (\Psi_N/2) = n\lambda \quad (2)$$

The equation (2) above speaks that, if the periodicity d increases, that is, at a point of reflection at the X-ray analyzing element 1 which is furthest from the X-ray radiation source P, the reflection angle $\Psi_N$ increases to such a value that the reflection angle $\Psi_1$ becomes smaller than the reflection angle $\Psi_2$. Considering $\Delta PL_1O_1$ and $\Delta Q1R_1O_1$, since $\Omega_o = -\Psi_1 + \angle Q1O_1R_1$ and, on the other hand, $\Omega_2 = \Psi_2 - \angle Q1O_1R_1$, selection of the reflection angles $\Psi_1$ and $\Psi_2$ and the angle $\angle Q1O_1R_1$ to respective appropriate values results in a reduction of the virtual convergent angle (divergent angle) $\Omega_2$, at which the diffracted X-ray beam B2 converges to a value smaller than the divergent angle $\Omega_o$. Accordingly, the radiant X-ray beam B1 generated from the X-ray radiation source P at a relatively great divergent angle $\Omega_o$ towards the artificial multi-layered grating 1 can impinge upon the specimen 2 at a relatively small virtual convergent angle (divergent angle) $\Omega_2$ and, therefore, the decrease of the intensity of the diffracted X-ray beam B2 can be suppressed to increase the intensity as compared with that afforded by the prior art X-ray diffraction analysis apparatuses.

In the practice of the present invention, during the X-ray diffraction analysis, it is necessary to cause the first diffracted X-ray beam B2 to be incident upon the specimen 2 in the form as diverged, by the following reason.

In order for the X-ray detector 3 to detect an increased intensity of the incident X-ray beam, it is necessary to cause the second diffracted X-ray beam B6 travelling towards the X-ray detector 3 to be converged at the X-ray detector 3 and, for this purpose, it is necessary that the X-ray beam B2 diffracted at the virtual curved surface 2b of the specimen 2 must be incident upon the X-ray detector 3 in the form as diverged. Also, since the composition of the specimen 2 more or less varies from one site to another, a sufficiently accurate analysis requires a somewhat wide area of the specimen 2 to be irradiated by the first diffracted X-ray beam B2 and, for this purpose, it is necessary as well that the first diffracted X-ray beam 82 must be incident upon the specimen 2 with the virtual convergent angle (divergent angle) $\Omega_2$ remaining great to a certain extent.

In contrast thereto, according to the present invention, the radiant X-ray beam B1 emitted from the X-ray radiation source P at the relatively large divergent angle $\Omega_0$ is diffracted by the artificial multi-layered grating 1 to provide the first diffracted X-ray beam B2 which is diverged, but has a reduced divergent angle $\Omega_2$ before they impinge upon the specimen 2, thereby making it possible to accomplish the analysis of the specimen 2 over a relatively large area thereof. Also, since the X-ray detector 3 detects the second diffracted X-ray beam B6 having the reduced divergent angle $\Omega_2$, the error of X-ray diffraction analysis can also be advantageously decreased considerably.

The artificial multi-layered grating 1 wherein the spacing of the lattice planes is varied along the surface thereof is disclosed in, for example, the Japanese Laid-open Patent Publication No. 63-61200, published in 1988, and Review of Scientific Instruments, Vol. 53(2), "NEW METHOD FOR FOCUSING X-RAYS AND GAMMA RAYS" (R. K. Smither), American institute of Physics, February 1982. However, any of these publications has failed to disclose the utilization of the first diffracted X-ray beam B2 allowed to diverge, but having the reduced divergent angle and differs from the present invention in that it allows the first diffracted X-ray beam B2 to be converged or parallel. Because of this, when an X-ray diffraction analysis is carried out subject to a specimen 2 having a relatively large area to be analyzed, the optical path along which the second diffracted X-ray beam B6 travel tends to be lengthened as discussed in connection with the prior art X-ray diffraction analysis apparatuses, accompanied by a reduction in intensity of the X-ray beam sensed by the X-ray detector. Accordingly, the use of the artificial multi-layered grating disclosed in the Japanese Laid-open Patent Publication No. 63-61200 or by R. K. Smither is ineffective to provide a sufficiently accurate analytical measurement.

According to the Japanese Laid-open Patent Publication No. 4-169898 which was published interim during the respective filing dates of our basic Japanese Patent Applications to which Convention priorities are claimed in the present application, there is discloses an artificial multi-layered grating of a type wherein the spacing of the lattice planes is varied along the surface thereof and, also, the application of such artificial multi-layered grating to the X-ray diffraction analysis. However, the artificial multi-layered grating disclosed in this publication has a reflective surface that is generally curved so as to occupy a portion of the parabola of revolution such that parallel beams are focused on a point of focus. The system disclosed therein therefore differs from the present invention in which the first diffracted X-ray beam B2 is converged and, therefore, the use of this artificial multi-layered grating in the X-ray diffraction analysis does not result in an improved measurement accuracy.

So far as the standard analyzing crystal wherein the periodicity d of the spacing of the lattice planes is fixed is concerned, Johann monochromator, Johansson monochromator and a logarithmically spirally curved monochromator are well known. Of these monochromators, Johann monochromator is limited in performance for use with a crystal having a short length and, therefore, in most cases, Johansson monochromator and the logarithmically spirally curved monochromator are generally utilized. However, the use of Johansson monochromator requires the crystal to be partially ground and is therefore difficult to use with the artificial multi-layered grating 1 having an extremely thin grating layer. Accordingly, the use of the logarithmically spirally curved monochromator is preferred in the X-ray diffraction analysis apparatus according to the present invention.

Figure 2:
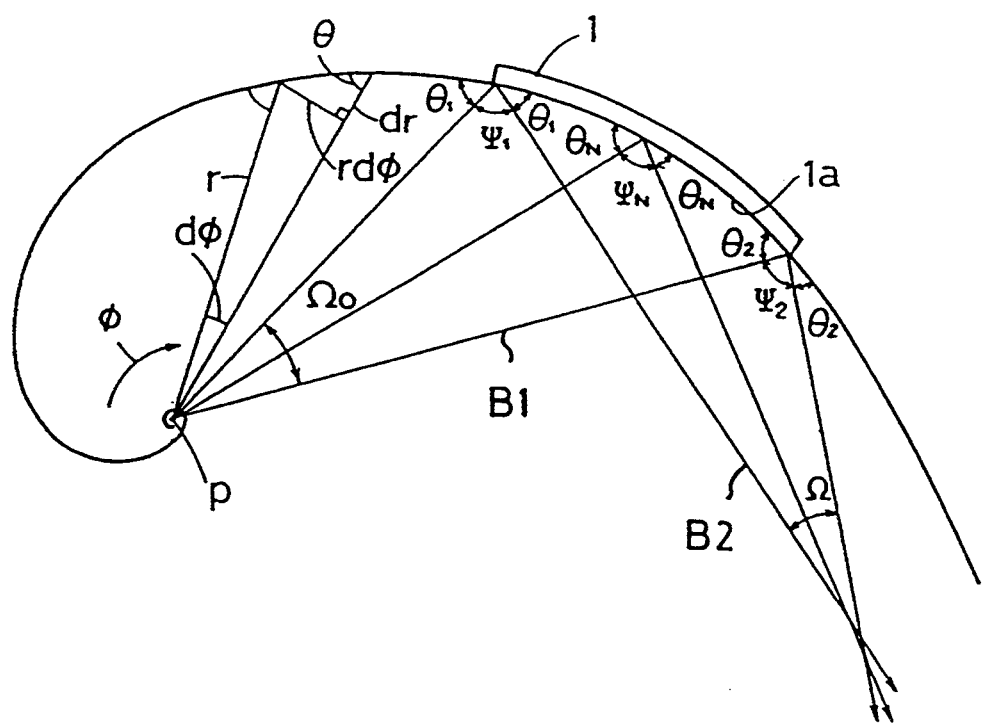
FIG. 2 is a side view of an artificial multi-layered grating showing the shape of a reflective surface thereof.

Referring to FIG. 2, the general equation representing the logarithmic spiral is expressed by the following equation (3) since, at any point on the reflective surface 1a, an equal incident angle $\theta_N$ is attained. The distance (radius vector) r from the X-ray radiation source P to the reflective surface 1a at the angle of inclination $\Phi$ is expressed by the following equation (4).

$$\cot \theta_N = (dr)/(r \cdot d\Phi) = m \qquad (3)$$

$$r = C_3 \cdot e^{m\Phi} \qquad (4)$$

wherein $C_3$ and m represent respective constants.

On the other hand, in the present invention, since the periodicity d of the spacing of the lattice planes increases as a point on the reflective surface 1a goes further away from the X-ray radiation source P, the incident angle $\theta$ on the artificial multi-layered grating 1 must be small. In view of this, as a result of intensive studies on the sectional configuration of the reflective surface 1a of the artificial multi-layered grating 1, the inventors have found that, when the radius vector r attains a value greater than the radius vector r given by the foregoing equation (4) with an increase of the angle of inclination $\Phi$, the incident angle $\theta_N$ becomes small and, based on this finding, the inventor could successfully determine a suitable configuration of the reflective surface 1a of the artificial multi-layered grating 1. In other words, when the radius vector r is expressed by a high order exponential function of the angle of inclination $\Phi$ as shown by the following equation (5), the incident angle $\theta_N$ becomes small with an increase of the angle of inclination $\Phi$.

$$r = c_1 \cdot e^{m_n \Phi} + \ldots + m_i \Phi + \ldots + m_1 \Phi \qquad (5)$$

wherein:
- r: Distance (Radius Vector) from the X-ray radiation source to the reflective surface at the angle of inclination $\Phi$,
- $\Phi$: Angle of inclination,
- $C_1$: Constant,
- $m_1$: Constant, and
- $m_2 \sim m_n$: Constant (However, at least one of these constants $m_2 \sim m_n$ is a positive constant.)

Accordingly, based on the system of polar coordinates expressed by the equation (5) above, the artificial multi-layered grating 1 advantageously utilizable in the practice of the present invention can be obtained.

As is well known to those skilled in the art, the artificial multi-layered grating i has a relatively large spacing of lattice planes with the periodicity thereof varying necessarily and, therefore, the resolution of X-rays is lower than that exhibited by a single crystal. However, in a preferred embodiment of the present invention, the analyzing crystal is disposed on the optical path extending from the X-ray radiation source P to the X-ray detector 3 as shown in FIG. 1 to render one of the X-ray beams B1, B2 and B6 to be monochromatic. This specific disposition of the analyzing crystal makes it possible to restore the lowered power of the artificial multi-layered grating 1 to resolve the energies thereby to ensure a decreased error of analytical measurement.

According to another preferred embodiment of the present invention, the analyzing crystal is disposed on the optical path extending between the specimen 2 to the X-ray detector 3 or from the X-ray radiation source P to the artificial multi-layered grating 1.

Again, as is well known to those skilled in the art, the artificial multi-layered grating 1 has a periodicity d of the spacing of the lattice plane that is larger than that of the analyzing crystal and, therefore, the incident angle $\theta$ tends to be small as can readily understood from the previously discussed Bragg's equation. For this reason, a continuous X-ray beam component (Bremsstrahlung X-rays) of a longer wavelength contained in the X-ray beam B1 undergoes a total reflection at the surface 1a of the artificial multi-layered grating 1 and the totally reflected continuous X-ray beam subsequently impinges upon the specimen 2 together with the first diffracted X-ray beam B2. This X-ray beam component of long wavelength forms the background of the second diffracted X-ray beam B6, resulting in a reduction in the resolving power, that is, the signal-to-noise ratio to such an extent that no accurate spectroanalytic measurement is possible with an extremely small quantity of impurities.

Accordingly, in a further preferred embodiment of the present invention, the use is made of a X-ray semitransparent mirror (half-mirror) on the optical path of the X-ray beams B1, B2 and B6 to allow a portion of the X-ray beams B1, B2 and B6 to undergo a total reflection thereby to reduce the X-ray beam component of long wavelength while only an X-ray beam component of short wave-length is allowed to pass therethrough. With the use of the X-ray semitransparent mirror, the disadvantage of the artificial multi-layered grating 1 which tend to reflect the X-ray beam component of long wavelength totally can advantageously be compensated for, and the background component can accordingly be reduced, permitting to ensure a reduced error of analytical measurement.

Preferably, according to the present invention, the X-ray semitransparent mirror referred to above is disposed on the optical path extending either from the X-ray radiation source P to the artificial multi-layered grating 1 or from the specimen 2 to the X-ray detector 3.

The basic structure and the principle of operation of the total reflection fluorescent X-ray analysis apparatus configured to accomplish the previously discussed object of the present invention will now be discussed with reference to FIG. 8 which illustrates another preferred embodiment of the present invention.

Even in the total reflection fluorescent X-ray analysis apparatus according to the present invention, the artificial multi-layered grating 1 is employed. As shown in FIG. 8(a), the artificial multi-layered grating 1 has a reflective surface 1a operable to diffract an X-ray beam B1 generated from the X-ray radiation source P and subsequently impinging upon the grating surface 1a at an incident angle $\theta$, thereby to provide a monochromatic X-ray beam. This artificial multi-layered grating 1 is so designed and so configured that the periodicity d of the spacing of the lattice planes progressively increases along the grating surface 1a. So far associated with the X-ray radiation source P, the periodicity d is chosen to have a value progressively increasing as the artificial multi-layered grating 1 goes away from the X-ray radiation source P as shown by the arrow 10.

Figure 9:
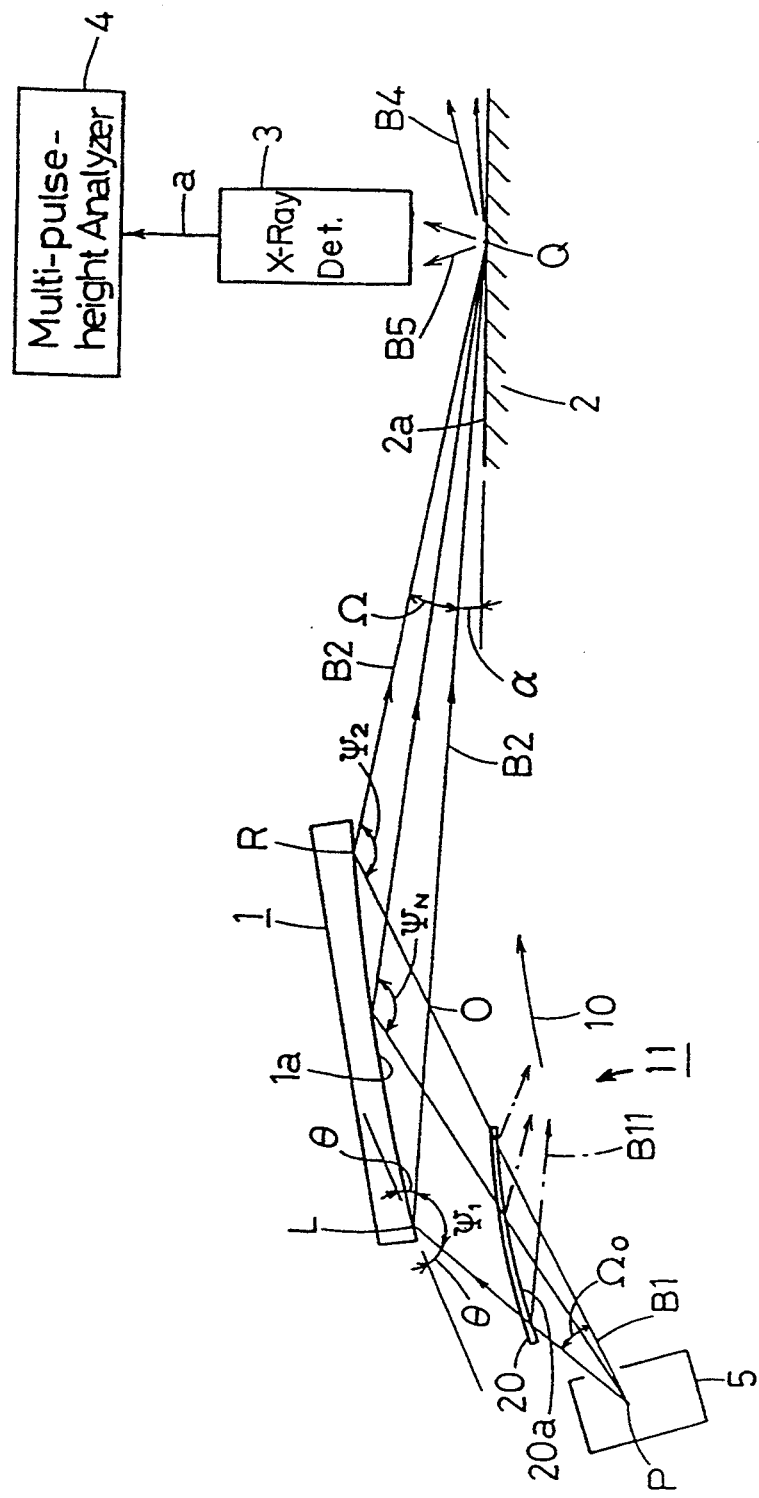
FIG. 9 is a schematic diagram showing the total reflection fluorescent X-ray analysis apparatus according to a fifth preferred embodiment of the present invention.

In view of the previously discussed equation (2), if the periodicity d increases, that is, at a point of reflection at the X-ray analyzing element 1 which is furthest from the X-ray radiation source P, the reflection angle $\Psi_N$ increases to such a value that the reflection angle $\Psi_1$ becomes smaller than the reflection angle $\Psi_2$ shown in FIG. 9. Considering $\triangle PLO$ and $\triangle QRO$, since $\angle LOP$ is equal to $\angle ROQ$ and the reflection angle $\Psi_1$ is smaller than the reflection angle $\Psi_2$, the convergent angle 0 becomes smaller than the divergent angle $\Omega o$. Accordingly, the radiation X-ray beam B1 generated from the X-ray radiation source P at a relatively great divergent angle $\Omega o$ towards the artificial multi-layered grating 1 can impinge upon the specimen 2 at a relatively small convergent angle (divergent angle) $\Omega_2$ and, therefore, the decrease of the intensity of the diffracted X-ray beam B2 can, while the incident angle $\alpha$ is maintained at a small value of about 0.05 to 0.20 degree, be suppressed to increase the intensity as compared with that afforded by the prior art total reflection fluorescent X-ray analysis apparatuses. Consequently, the accuracy of the spectroanalytic measurement can advantageously be improved.

The artificial multi-layered grating 1 wherein the spacing of the lattice planes is varied along the surface thereof is disclosed in, for example, the Japanese Laid-open Patent Publication No. 63-81200, published in 1988, and Review of Scientific Instruments, Vol. 53(2), "NEW METHOD FOR FOCUSING X-RAYS AND GANNA RAYS" (R. K. Smither), American institute of Physics, February 1982. However, any of these publications has failed to disclose the applicability of the artificial multi-layered grating to the total reflection fluorescent X-ray analysis to reduce the decrease of the intensity of the diffracted X-ray beam B2 while the incident angle $\alpha$ is maintained at such a small value as described above.

Thus, even in the total reflection fluorescent X-ray analysis apparatus embodying the present invention, it is preferred to use the artificial multi-layered grating 1 having the reflective surface 1a so designed and so configured to satisfy the system of polar coordinates expressed by the following equation (6).

$$r = C_2 \cdot e^{k_n \Phi^n + \ldots + k_i \Phi^i + \ldots k_1 \Phi} \quad (6)$$

wherein:
- r: Distance (Radius Vector) from the X-ray radiation source to the reflective surface at the angle of inclination $\Phi$,
- $\Phi$: Angle of inclination,
- $C_1$: Constant,
- $k_1$: Constant, and
- $k_2 \sim k_n$: Constant (However, at least one of these constants $k_2 \sim k_n$ is a positive constant.)

Figure 4:
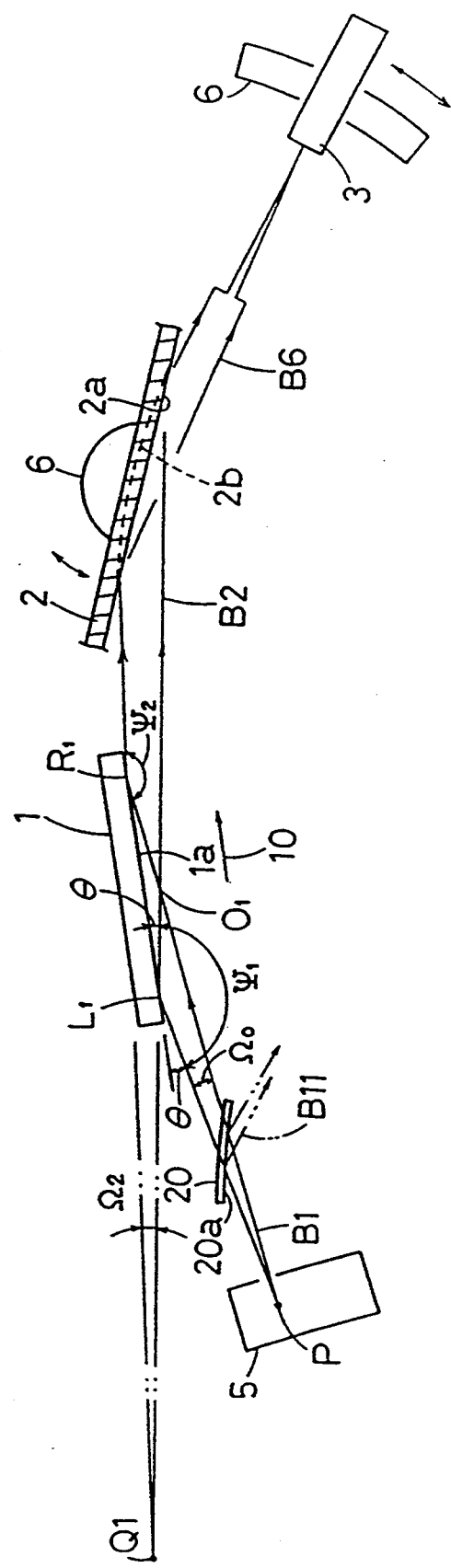
FIG. 4 is a schematic diagram showing the X-ray diffraction analysis apparatus according to a third preferred embodiment of the present invention.
Figure 5:
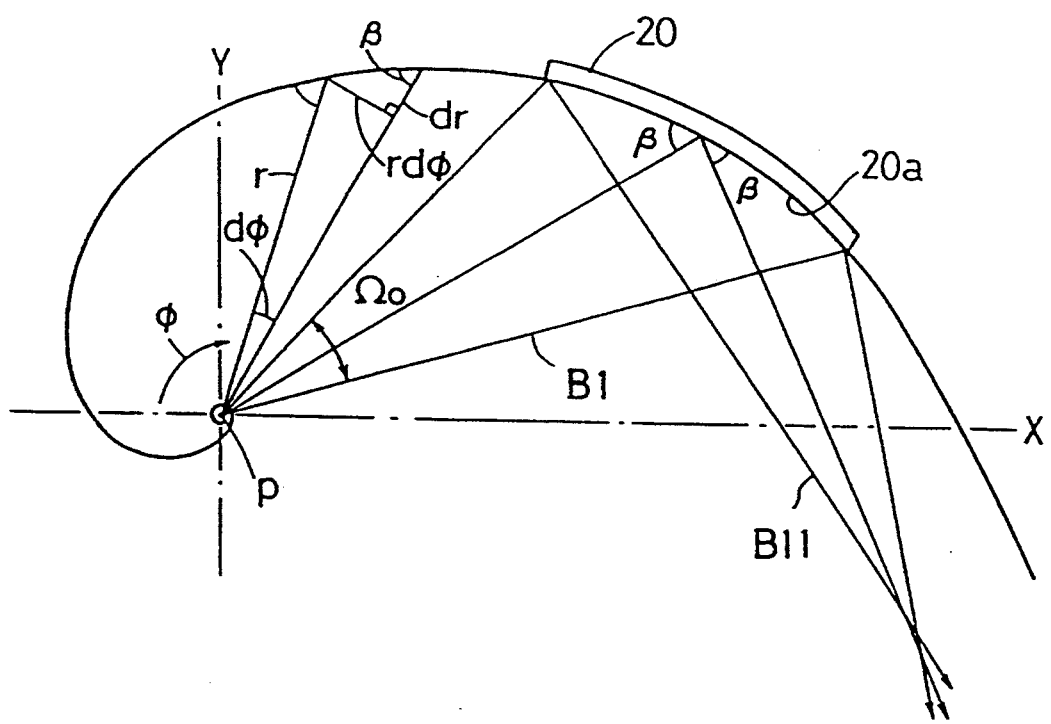
FIG. 5 is a side view of a semitransparent mirror showing the shape thereof.

Accordingly, in a further preferred embodiment of the present invention, the use is made of a X-ray semitransparent mirror operable to allow a portion of the X-ray beams to undergo a total reflection thereby to reduce the X-ray beam component of long wavelength while only an X-ray beam component of short wavelength is allowed to pass therethrough which is shown in FIG. 4.

Preferably, according to the present invention, the X-ray semitransparent mirror referred to above is disposed on the optical path extending either from the X-ray radiation source P to the artificial multi-layered grating 1 or from the grating 1 to the specimen 2.

Detailed Description of Embodiments

Hereinafter, various embodiments in which the present invention is applied to the analysis of diffracted X-ray beams will be described in detail with reference to the accompanying drawings.

Referring now to FIG. 1 showing the first preferred embodiment of the present invention, the artificial multi-layered grating 1, which is utilized as a monochromator, has a reflective surface 1a slightly curved inwardly. In the illustrated embodiment, the specimen 2 and the X-ray detector 3 used to detect the second diffracted X-ray beam B6 which has been diffracted by the specimen 2 are rotated about the center of a surface 2a of the specimen 2 at an angular velocity ratio of 1:2 by means of a goniometer 6. The X-ray detector 3 operable to detect the second diffracted X-ray beam B6 also calculates the incident angle of the first diffracted X-ray beam B2 on the specimen 2 to provide an indication of the periodicity of the spacing of the lattice planes of the specimen 2, thereby completing the analysis of the specimen 2. The specimen 2 is in the form of a compacted mass of powder.

Since the other structural features of the X-ray diffraction analysis apparatus than that described above have been described under the DETAILED DESCRIPTION OF THE INVENTION which has been set forth hereinbefore, the details thereof will not be reiterated for the sake of brevity.

Assuming that the diffracted X-ray beam B2 incident upon the specimen 2 converges at the virtual X-ray collecting point Q1, and since the diffracted X-ray beam B2 is required to be nearly parallel rays, the convergent angle (divergent angle) $\Omega_2$ at which the diffracted X-ray beam B2 converges at the X-ray collecting point Q1 is chosen to be, for example, about 0.5 degree. Since in the case of a plate crystal made of the standard single crystal, the divergent angle no at which the X-ray beam is generated from the X-ray radiation source P must necessarily be chosen to be about 0.5 degree as well, it is not possible to secure a sufficiently increased intensity of the diffracted X-ray beam B2.

In contrast thereto, in the illustrated embodiment of the present invention, the periodicity d of the spacing of the lattice planes of the artificial multi-layered grating 1 is so configured as to progressively increase along the grating surface 1a and, therefore, the divergent angle $\Omega_o$ becomes greater than the virtual convergent angle (virtual divergent angle) $\Omega_2$ as discussed under the DETAILED DESCRIPTION OF THE INVENTION. By way of example, if the divergent angle $\Omega_o$ is 5 degrees, the convergent angle $\Omega_2$ can be set to 0.5 degree. Therefore, it is possible to intensify the diffracted X-ray beam B2 while the convergent angle $\Omega_2$ is maintained at 0.5 degree, making it possible to reduce the error in spectroanalytic measurement.

The periodicity d of the spacing of the lattice planes the X-ray analyzing element 1 is determined by the following manner. In the first place, the virtual convergent angle $\Omega_2$ is determined, followed by determination of the wavelength $\lambda$ of the first diffracted monochromatic X-ray beam B2 used during the spectroanalytic measurement. Then, the respective angles of reflection $\Psi_1$ and $\Psi_2$ at opposite ends of the artificial multi-layered grating 1 are determined, followed by determination of the respective periodicities $d_1$ and $d_2$ at points $L_1$ and $R_1$ adjacent the opposite ends of the artificial multi-layered grating 1. Since the incident angle $\theta$ in the Bragg's equation is generally small at a point between the points $L_1$ and $R_1$, and if it is varied approximately linearly, the wavelength of the diffracted X-ray beam B2 becomes a substantially constant value with sufficient accuracy.

The sectional configuration of the reflective surface 1a of the artificial multi-layered grating 1 will now be discussed. Referring to FIG. 2, the reflective surface 1a has a configuration determined by the following equation (7).

$$r = C_1 \cdot e^{m_3 \Phi^3 + m_2 \Phi^2 + m_1 \Phi} \quad (7)$$

wherein $m_1$, $m_2$ and $m_3$ represent respective positive constants.

By way of example, when $\Omega_o = 1$ degree and $\Omega = 0.5$ degree, and if the radius vector r and the angle of inclination $\Phi$ are expressed in units of mm and radian, respectively, and the line passing across the origin P and dividing the divergent angle $\Omega_o$ into two equal parts is taken as a base line, and again if the coordinates of the points Q1, $L_1$ and $R_1$ are assumed (60.2, 3.039), (38.52, $-0.00873$) and (102.13, 0.00873), respectively, the parameters $C_1$, $m_3$, $m_2$ and $m_1$ take respective value of 60.0, 275, 583 and 55.82. In such case, the length of the artificial multi-layered grating 1 as measured in the direction shown by the arrow 10 is 64 mm, the periodicity $d_1$ is 29.3 Å and the periodicity $d_2$ is 42.3 Å.

It is to be noted that, in the practice of the present invention, the radius vector r may be either a second order exponential function or a fourth or higher order exponential function.

As discussed above, when the radius vector r is expressed by a high order exponential function, the reflective surface 1a of the artificial multi-layered grating 1 employable in the practice of the present invention can represent the required smoothly inwardly curved profile. Since at this time the periodicity d of the spacing of the lattice planes suffices to be linearly varied, the artificial multi-layered grating 1 can easily be manufactured by the method which will be described later.

Figure 3:
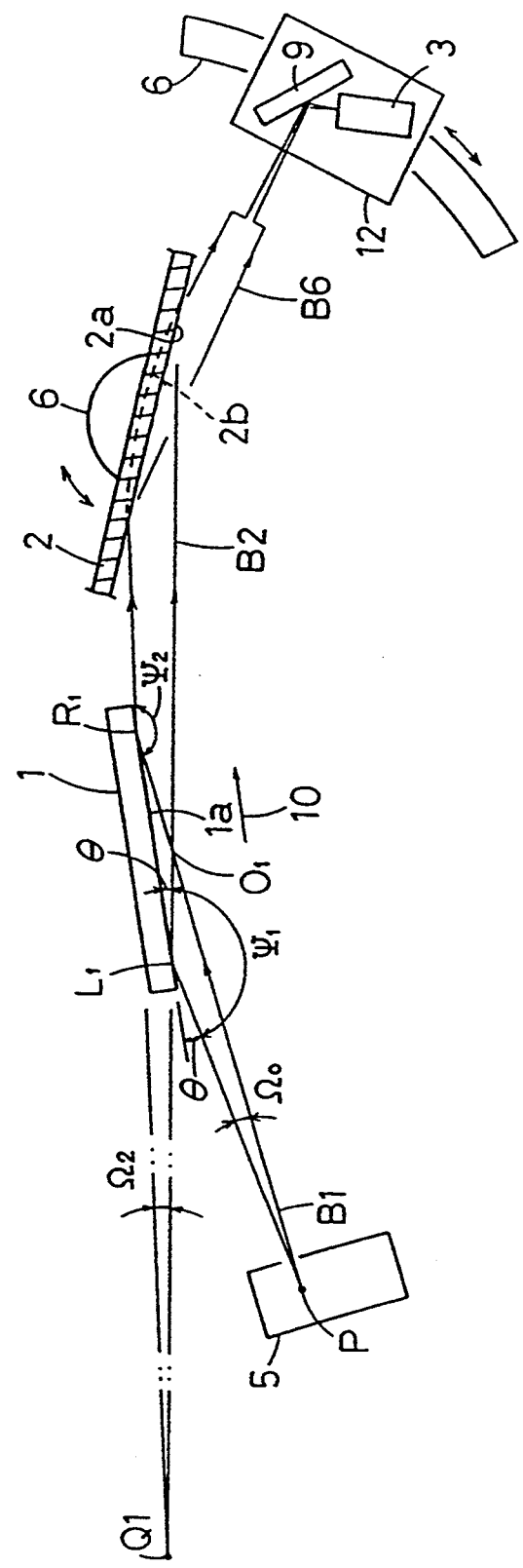
FIG. 3 is a schematic diagram showing the X-ray diffraction analysis apparatus according to a second preferred embodiment of the present invention.

FIG. 3 illustrates the second preferred embodiment of the present invention. In this embodiment of FIG. 3, the analyzing crystal 9 is disposed on the optical path between the specimen 2 and the X-ray detector 3. This analyzing crystal 9 is used to render the second diffracted X-ray beam B6 to be monochromatic and is mounted on a movable carrier 12 together with the X-ray detector 3 for angular movement together therewith by means of the goniometer 6 at an angular velocity which is twice that of the angular movement of the specimen 2.

The use of the analyzing crystal 9 for rendering the second diffracted X-ray beam B6 to be monochromatic is effective to compensate for a low resolution power of the artificial multi-layered grating 1 as discussed under the DETAILED DESCRIPTION OF THE INVENTION, ensuring a further improved accuracy of spectroanalytic measurement.

As an alternative to the above described second preferred embodiment of the present invention, the analyzing crystal 9 may be disposed on the optical path between the X-ray radiation source P and the artificial multi-layered grating 1. In any event, the present invention allows the analyzing crystal 9 to be disposed anywhere on the entire optical path extending between the X-ray radiation source P and the X-ray detector 3.

The third preferred embodiment of the present invention will now be described with particular reference to FIG. 4.

Referring to FIG. 4, an X-ray semitransparent mirror 20 is disposed on the optical path along which the X-ray beam B1 emitted from the X-ray radiation source P travels towards the artificial multi-layered grating 1. This X-ray semitransparent mirror 20 is operable to allow a component B11 of long wavelength of the X-ray beam B1 generating from the X-ray radiation source P to undergo a total reflection as shown by the single-dotted chain line to reduce that long wavelength component B11 while permitting a short wavelength component of the X-ray beam to pass therethrough. The X-ray semitransparent mirror 20 is formed by coating a light metal such as, for example, aluminum to a thickness of, for example, 200 Å over a reflective surface 20a of a film made of synthetic resin of low density (specific gravity) such as, for example, polypropylene (having a density of about 1 g/cm$^3$) or polyester (having a density of about 1.3 g/cm$^3$).

In this embodiment of FIG. 4, the divergent angle $\Omega$o is chosen to be about 10 degree, and in order to render the incident angle $\beta$ of the X-ray beam B1 upon the X-ray semitransparent mirror 20 to be constant, the X-ray semitransparent mirror 20 has the reflective surface 20a which is curved logarithmically spirally. It is to be noted that the incident angle $\beta$ upon the X-ray semitransparent mirror 20 is set to about 0.22 degree where an analyzing element is any of titanium (Ti), iron (Fe) and nickel (Ni). The logarithmic spiral curvature of the reflective surface 20a of the X-ray semitransparent mirror 20 is expressed by the following equations (8) and (9).

$$\cot \beta = (dr)/(r \cdot d\Phi) = n \quad (8)$$

$$r = C \cdot e^{n\Phi} \quad (9)$$

wherein n represents a constant.

However, since the artificial multi-layered grating 1 has a periodicity d of the spacing of the lattice plane that is longer than that of the analyzing crystal, there is a problem in that the continuous X-ray beam component of a longer wavelength contained in the X-ray beam B1 which has been described as undergoing a total reflection at the surface 1a of the artificial multi-layered grating 1 in the first embodiment of the present invention will form the background, resulting in a reduction in the resolving power, that is, the poor signal-to-noise ratio to such an extent that no accurate spectroanalytic measurement is possible with an extremely small quantity of impurities.

In view of the above, in the third preferred embodiment of the present invention shown in FIG. 4, the use of the X-ray semitransparent mirror 20 is effective to allow the long wavelength component B11 of the X-ray beam B1 generated from the X-ray radiation source P to undergo a total reflection thereby to reduce or substantially eliminate the long wavelength X-ray component while allowing only the short wavelength X-ray component to eventually impinge upon the artificial multi-layered grating 1. Accordingly, even though the artificial multi-layered grating 1 of a type likely to cause the long wavelength X-ray to undergo the total reflection is employed, the diffracted X-ray beam B2 is substantially free from the long wavelength component and, therefore, the continuous X-ray beam hardly enters the X-ray detector 3, making it possible to improve the accuracy of spectroanalytic measurement.

So far as shown in FIG. 4, the X-ray semitransparent mirror 20 has been shown as disposed on the optical path extending from the X-ray radiation source P to the artificial multi-layered grating 1. However, in the practice of the present invention, the X-ray semitransparent mirror 20 may be disposed on the optical path extending from the specimen 2 to the X-ray detector 3 to reduce the long wavelength component of the second diffracted X-ray beam B2 by total reflection.

The artificial multi-layered grating 1 advantageously employed in the present invention can be manufactured by the method which will now be described with reference to FIGS. 6(a) to 6(c).

Referring to FIG. 6, a generally rectangular substrate 1b having flat surfaces opposite to each other such as, for example, a silicon wafer, is first prepared and, then, a film-like deposit material 6w made of tungsten and a film-like deposit material 6si made of silicon are placed on the substrate 1b at a location adjacent a right-hand end 1R and intermediate the width thereof. Thereafter, as shown in FIG. 6(a), the tungsten deposit material 6w is evaporated in a vacuum chamber to form a tungsten thin film 1w on the surface of the substrate 1b, followed by, as shown in FIG. 6(b), evaporation of the silicon deposit material 6si in the vacuum chamber to form a silicon thin film 1si so as to overlay the tungsten thin film 1w, thereby to complete a single cycle of evaporation process. This cycle of evaporation process is repeated a required number of times to complete the artificial multi-layered grating 1 shown in FIG. 6(c).

During the execution of the evaporation, since the deposit materials 6w and 6si are, as shown in FIG. 6(a) and 6(b), positioned on the substrate 1b at the location adjacent the right-hand end 1R and intermediate the width thereof, each of the resultant thin films 1w and 1si has a maximum thickness at the right-hand end 1R of the substrate 1b and a minimum thickness at the opposite, left-hand end 1L of the substrate with a generally intermediate portion thereof having a progressively varying thickness, i.e., a progressively increasing periodicity $d_N$ from the left-hand end 1L towards the right-hand end 1R along the surface of the substrate as best shown in FIG. 6(c). It is however to be noted that, although the resultant reflective surface 1a may be somewhat outwardly curved, the reflective surface 1a represents a smoothly inwardly curved surface when the artificial multi-layered grating 1 is eventually bent.

FIG. 7 illustrates another method of making the artificial multi-layered grating 1. In the practice of the method shown in FIG. 7, a well-known chemical evaporation process is employed and, for the sake of brevity, only a brief discussion thereof is herein given.

Referring now to FIG. 7, a horizontally movable mask 7 positioned immediately below an undersurface of the substrate 1b made of silicon. The movable mask 7 has a narrow slit 7a defined therein. Positioned beneath the slitted mask 7 is a gas chamber 8 filled with a gaseous mixture of gallium (Ga) compound and arsenic (As). While the mask 7 is slowly moved leftwards as viewed therein, a gaseous compound of indium In is supplied into the gas chamber 8 while the latter is concurrently vented. In this way, not only is a thin film made up of atoms of different diameters formed on the undersurface of the substrate 1b, but the resultant thin film represents a condition ($In_xGa_{1-x}As$) wherein the proportions of gallium and indium contained in the In-Ga-As compound deposited on the undersurface of the substrate 1b progressively varies from the right-hand end 1R towards the left-hand end 1L and, therefore, the periodicity $d_2$ of the spacing of the lattice plane at the right-hand end 1R of the substrate 1b becomes greater than the periodicity $d_1$ thereof at the left-hand end 1L.

Figure 10:
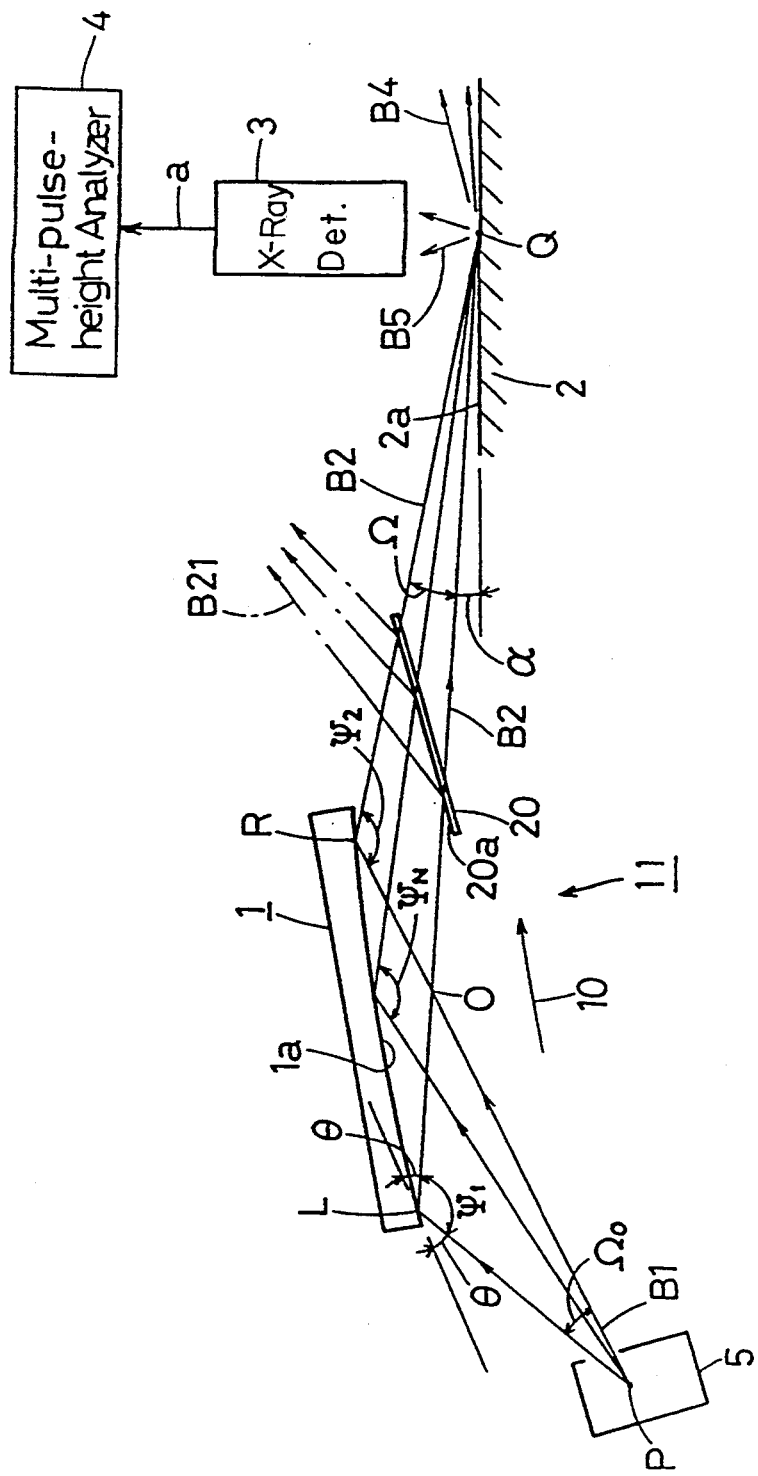
FIG. 10 is a schematic diagram showing the total reflection fluorescent X-ray analysis apparatus according to a sixth preferred embodiment of the present invention.
Figure 11:
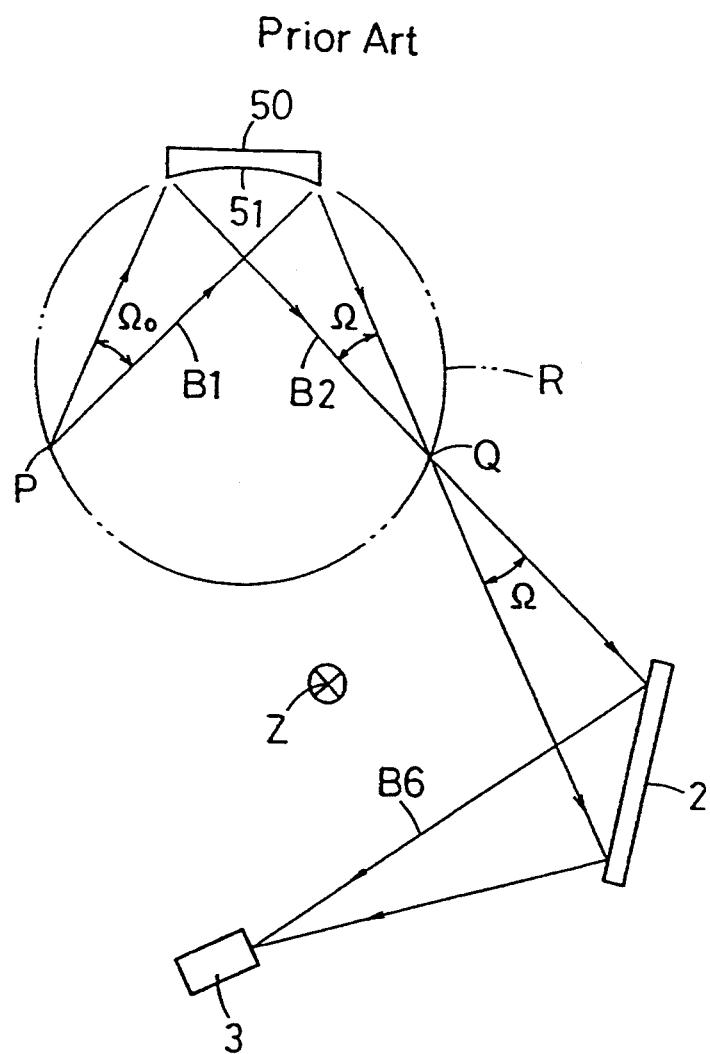
FIG. 11 is a schematic diagram showing the prior art X-ray diffraction analysis apparatus.

Hereinafter, some embodiments in which the present invention is applied to the total reflection fluorescent X-ray analysis will be described in detail with reference to FIGS. 8 to 10.

Referring first to FIGS. 8(a) and 8(b) showing the fourth preferred embodiment of the present invention, the artificial multi-layered grating 1 forming a part of an irradiation device 11 has a reflective surface 1a operable to diffract the X-ray beam B1, generated from the X-ray radiation source P and incident thereon at an incident angle $\theta_N$, to render the X-ray beam B1 to be monochromatic. As is the case with that described with reference to FIG. 6(c), the periodicity $d_N$ of the spacing of the lattice planes of the artificial multi-layered grating 1 shown in FIGS. 8(a) and 8(b) is so chosen as to progressively increase along the reflective surface 1a thereof. In terms of the relationship with the X-ray radiation source P shown in FIG. 8(a), this periodicity $d_N$ is so chosen as to increase as the distance from the X-ray radiation source P increases progressively in the direction shown by the arrow 10. By way of example, if the artificial multi-layered grating 1 has a length (as measured in the direction shown by the arrow 10) of 40 millimeters, the periodicity d at the left-hand end of the artificial multi-layered grating 1 and that at the right-hand end thereof are so chosen as to be 50 Å and 72 Å, respectively.

As best shown in FIG. 8(b), the artificial multi-layered grating 1 has the reflective surface 1a which is slightly curved inwardly representing a generally toroidal shape in a direction conforming to the direction shown by the arrow 10 and also in a direction perpendicular to the direction of the arrow 10, so that not only the X-ray beam B1 travelling in a plane parallel to the sheet of the drawing of FIG. 8(a), but also that travelling in a plane perpendicular to the sheet of the drawing of FIG. 8(a) can be converged. The diffracted X-ray beams B2 diffracted by the reflective surface 1a shown in FIG. 8(a) impinge upon the X-ray collecting point Q defined on the specimen 2 such as, for example, a silicon wafer, at a small incident angle $\alpha$ of, for example, 0.05 to 0.20 degree.

The diffracted X-ray beams (exciting X-ray beams) incident upon the specimen 2 is in part undergoing a total reflection to provide a reflected X-ray beam B4 while the remaining X-ray beam excites the specimen to cause the elements forming the specimen 2 to emit fluorescent X-ray beams B5 peculiar to these specimen elements. The fluorescent X-ray beams B5 emitting from the specimen 2 are subsequently detected by the X-ray detector 3 disposed in face-to-face relationship with the specimen surface 2a. The X-ray detector 3 then determines the intensity of the fluorescent X-ray beams B5 and provides a detection signal a which is subsequently fed to a multi-pulse-height analyzer 4 for providing X-ray spectra of interest.

Since the other structural features of the total reflection fluorescent X-ray analysis apparatus than that described above have been described under the BACKGROUND OF THE INVENTION which has been set forth hereinbefore, the details thereof will not be reiterated for the sake of brevity.

Figure 12:
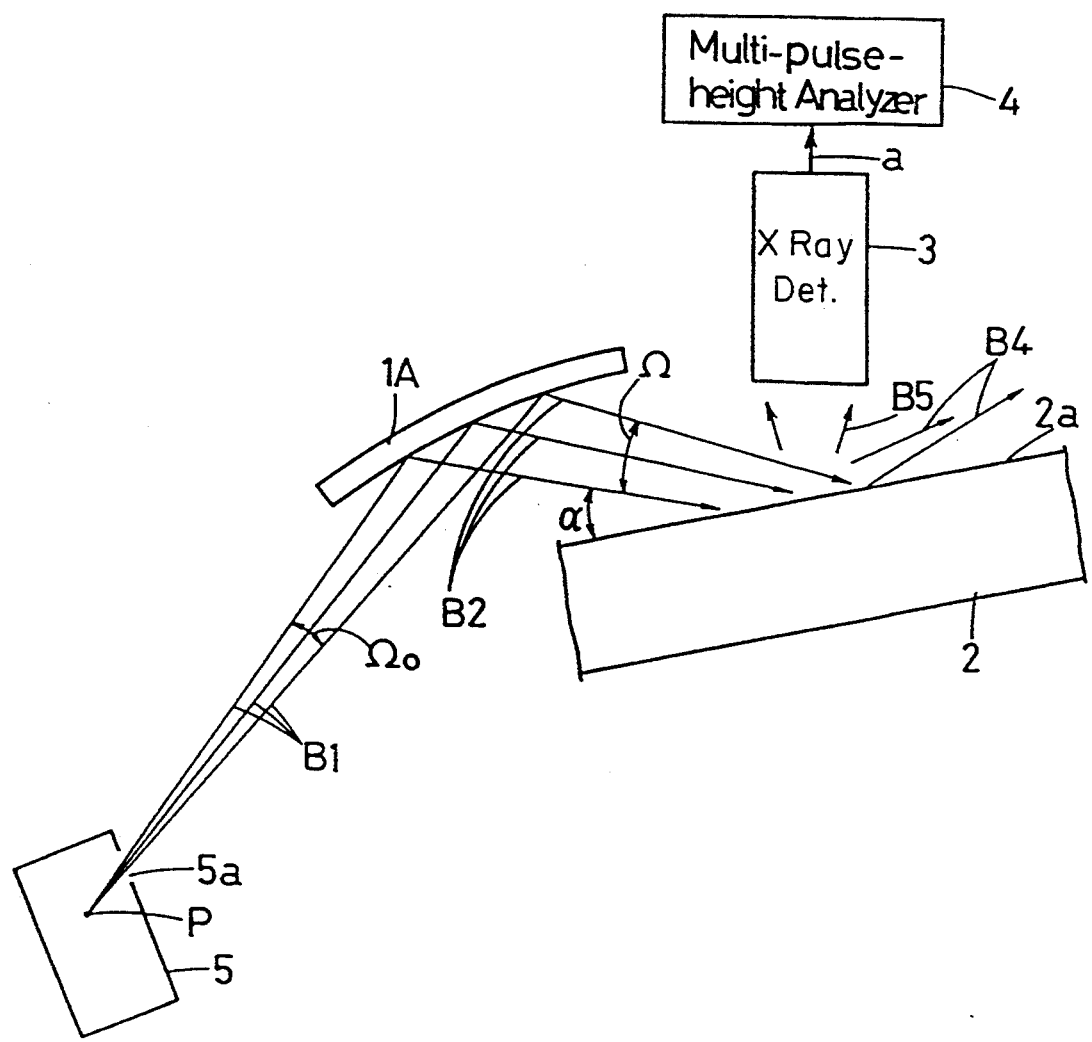
FIG. 12 is a schematic diagram showing the prior art total reflection fluorescent X-ray analysis apparatus.

In the above described total reflection fluorescence X-ray analysis apparatus, as hereinbefore discussed, since the incident angle $\alpha$ of the diffracted X-ray beam B2 is extremely small, the convergent angle $\Omega$ must be chosen to be of a value smaller than the range of the permissible incident angle $\alpha$ which is, for example, 0.05 to 0.2 degree. Accordingly, with the prior art curved analyzing crystal 1A shown in FIG. 12, since the convergent angle $\Omega$ and the divergent angle $\Omega_o$ become equal to each other, the divergent angle $\Omega_o$ must be reduced and, therefore, the intensity of the excitation X-ray beam (diffracted X-ray beam) incident on the specimen 2 tends to be weakened.

Figure 8:
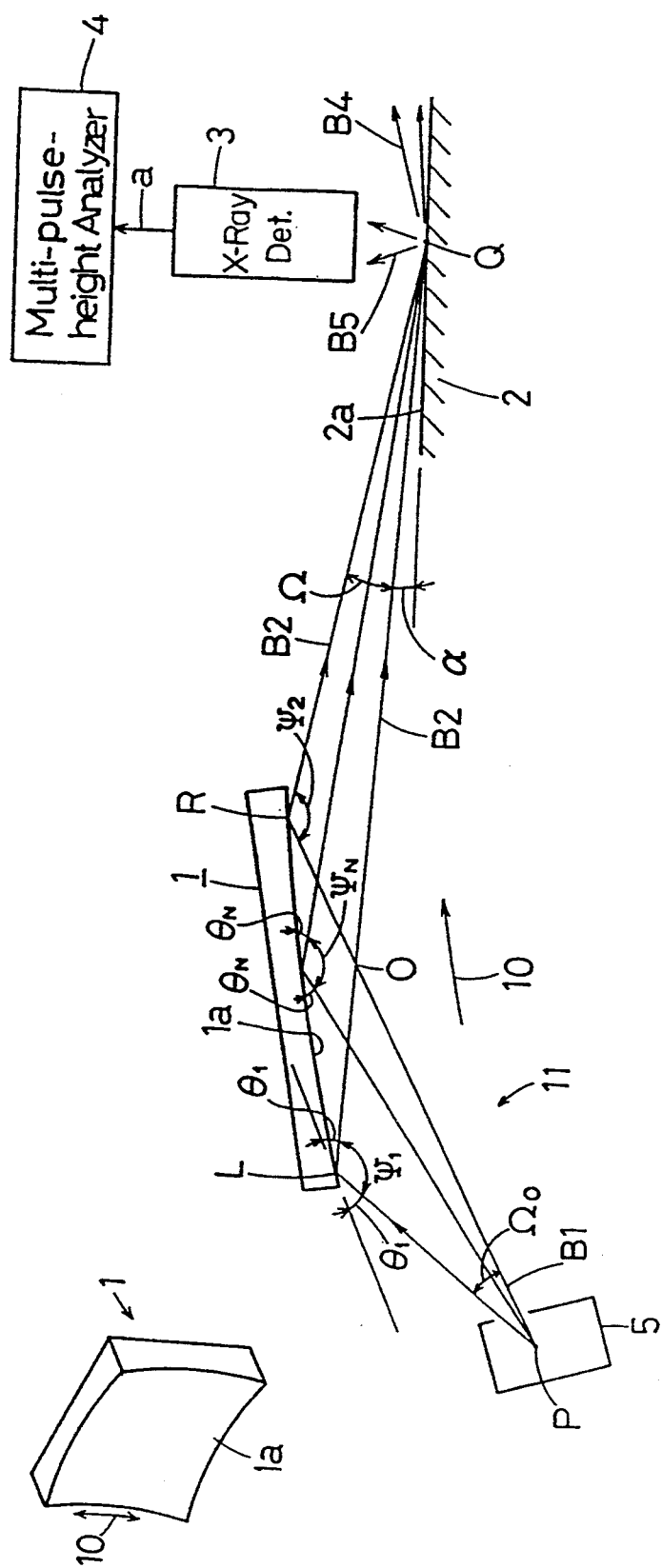
FIG. 8(a) is a schematic diagram showing a total reflection fluorescent X-ray analysis apparatus according to a fourth preferred embodiment of the present invention.
FIG. 8(b) is a perspective view showing the artificial multi-layered grating.

In contrast thereto, in the illustrated embodiment of the present invention, the periodicity $d_N$ (FIG. 6(c)) of the spacing of the lattice planes of the artificial multi-layered grating 1 shown in FIG. 8 is so configured as to progressively increase along the grating surface 1a and, therefore, the divergent angle $\Omega_o$ becomes greater than the convergent angle $\Omega$ as discussed under the DETAILED DESCRIPTION OF THE INVENTION. By way of example, if the divergent angle $\Omega_o$ is 1 degrees, the convergent angle $\Omega$ can be set to 0.1 degree. Therefore, it is possible to intensify the exciting X-ray beam (diffracted X-ray beam) B2 while the convergent angle $\Omega$ is maintained at a value small of 0.1 degree, making it possible to reduce the error in spectroanalytic measurement.

The periodicity d of the spacing of the lattice planes of the artificial multi-layered grating 1 is determined by the following manner.

In the first place, based on the perspective in which the total reflection takes place, the incident angle $\alpha$ and the convergent angle $\Omega$ are determined, followed by determination of the wavelength $\lambda$ of the first diffracted monochromatic X-ray beam B2 used during the spectroanalytic measurement. Then, the respective angles of reflection $\Psi_1$ and $\Psi_2$ at opposite ends of the artificial multi-layered grating 1 are determined, followed by determination of the respective periodicities $d_1$ and $d_2$ at points $L_1$ and $R_1$ adjacent the opposite ends of the artificial multi-layered grating 1. Since the incident angle $\theta$ in the Bragg's equation is generally small at a point between the points L and R, and if it is varied approximately linearly, the diffracted X-ray beam B2 can converge at the X-ray collecting point Q with sufficient accuracy.

The sectional configuration of the reflective surface 1 of the artificial multi-layered grating 1 will now be discussed. Referring to FIG. 2, the reflective surface 1a has a configuration determined by the following equation (10).

$$r = C_2 \cdot e^{k_2 \Phi^2 + k_1 \Phi} \tag{10}$$

wherein $C_2$ is a constant, and $k_2$ and $k_1$ represent respective positive constants.

By way of example, when $\Omega_o = 1$ degree and $\Omega = 0.37$ degree, and if the radius vector r and the angle of inclination $\Phi$ are expressed in units of mm and radian, respectively, and the line passing across the origin P and dividing the divergent angle $\Omega_o$ into two equal parts is taken as a base line, and again if the coordinates of the points Q, L and R are assumed (294, 0.0319), (52.5, −0.0873) and (117.2, 0.00873), respectively, the constants $C_2$, $k_2$ and $k_1$ take respective value of 76.47, 327 and 46.05. In such case, the length of the artificial multi-layered grating 1 as measured in the direction shown by the arrow 10 is 65 mm, the periodicity $d_1$ is 25.9 Å and the periodicity $d_2$ is 33.3 Å.

It is to be noted that, where the convergent angle $\Omega$ tends to become such a large value (0.37 degree) as discussed above, the use may be made of any known slit between the artificial multi-layered grating 1 and the specimen 2 to regulate the convergent angle $\Omega$ to be of a value not greater than 0.1 degree. In other words, only a portion of the artificial multi-layered grating 1 may be employed effectively.

It is also to be noted that, in the practice of the present invention, the radius vector r may be a high order exponential function of the angle of inclination $\Phi$ which is equal to or higher than the third order.

As discussed above, when the radius vector r is expressed by a high order exponential function of the angle of inclination $\Phi$, the reflective surface 1a of the artificial multi-layered grating 1 employable in the practice of the present invention can represent the required smoothly inwardly curved profile. Since at this time the periodicity $d_N$ of the spacing of the lattice planes suffices to be linearly varied, the artificial multi-layered grating 1 can easily be manufactured in the above described manner.

FIG. 9 illustrates the fifth preferred embodiment of the present invention. In this embodiment of FIG. 9, the irradiation device 11 includes the X-ray semitransparent mirror 20 disposed on the optical path between the X-ray radiation source P and the artificial multi-layered grating 1 and along which the X-ray beam generated from the X-ray radiation source P travels towards the artificial multi-layered grating 1. This X-ray semitransparent mirror 20 operates and is structured in a manner similar to that employed in the third embodiment of the present invention shown in and described with reference to FIG. 4.

Since the fluorescent X-ray beam B5 shown in FIG. 9 is generated as a result of excitation of atoms of the specimen 2 upon impingement of the diffracted X-ray beam B2 which is the exciting X-ray beam, a characteristic X-ray beam (fluorescent X-ray beam B5) peculiar to the element to be analyzed has a wavelength longer than that of the diffracted X-ray beam B2. For this reason, if a long wavelength component (continuous X-ray beam) is included in the exciting X-ray beam (diffracted X-ray beam B2), the long wavelength component will constitute a background of the fluorescent X-ray beam B5 to such an extent as to result in a reduction in spectroanalytic accuracy.

In contrast thereto, with the use of the X-ray semitransparent mirror such as accomplished in the present invention, this X-ray semitransparent mirror 20 operates to allow the long wavelength component B11 of the X-ray beam B1 emitted from the X-ray radiation source P to undergo a total reflection as shown by the single-dotted chain line to reduce or substantially eliminate that long wavelength component B11 while permitting a short wavelength component of the X-ray beam to pass therethrough. Accordingly, even if the artificial multi-layered grating 1 which may totally reflect a long wave component is utilized, the second diffracted X-ray beam B2 is substantially free from the long wavelength component and, therefore, the continuous X-ray beam hardly enters the X-ray detector 3, making it possible to improve the accuracy of spectroanalytic measurement.

In describing the foregoing embodiment of FIG. 9, the X-ray semitransparent mirror 20 has been shown as disposed on the optical path extending between the X-ray radiation source P and the artificial multi-layered grating 1. However, as an alternative to the above described embodiment (FIG. 10) of the present invention, the X-ray semitransparent mirror 20 may be disposed on the optical path between the artificial multi-layered grating 1 and the specimen 2, as shown in FIG. 10, so that the long wavelength component B21 of the diffracted X-ray beam B2 can be reflected totally to disappear. It is however to be noted that, since the convergent angle $\Omega$ of the diffracted X-ray beam B2 employed in the sixth embodiment of the present invention is extremely small, the X-ray semitransparent mirror 20 need not have a logarithmically spirally curved reflective surface and, accordingly, the reflective surface 20a of the X-ray semitransparent mirror 20 referred to above is formed flat or substantially flat.

It is also to be noted that, in the foregoing embodiment, the reflective surface 20a of the X-ray semitransparent mirror 20 has been described as coated with a metal layer, the X-ray semitransparent mirror 20 employable in the practice of the present invention need not always require the metal coating an the reflective surface 20a.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Far example, those skilled in the art may conceive a possibility of combining the respective embodiments of the present invention shown in FIGS. 3 and 4 to provide the X-ray diffraction analysis apparatus wherein both of the X-ray semitransparent mirror 20 shown in FIG. 4 and the analyzing crystal 9 shown in FIG. 3 are concurrently employed.

Accordingly, such changes and modifications are, unless they depart from the scope of the present inven-

What is claimed is:

1. X-ray analysis apparatus for providing an indication of the spacing of lattice planes of a substance forming a specimen based on the angle of diffraction of a diffracted x-ray beam, diffracted by the specimen, and the wavelength thereof, said apparatus comprising:

an x-ray radiation source for generating an x-ray beam;

an artificial multi-layered grating having a reflective surface of a predetermined profile and comprising a plurality of lattice planes located on a substrate, said lattice planes having a periodicity respectively increasing in the thickness from one end to an opposite end in a direction away from said x-ray radiation source such that said x-ray beam generated by said source and incident thereon at said one end is diffracted to provide a monochromatic diffracted x-ray beam in an oblique direction at said opposite end, said predetermined profile causing the monochromatic diffracted x-ray beam to be divergent and incident on the specimen at a reduced divergent angle so as to increase the intensity of said monochromatic x-ray beam incident upon the specimen;

an x-ray detector for receiving a second diffracted x-ray beam diffracted by the specimen; and a goniometer for rotating the specimen and the x-ray detector at an angular velocity ratio of 1:2 relative to each other.

2. The X-ray analysis apparatus as claimed in claim 1, wherein said predetermined profile is defined by a system of polar coordinations represented by the following equation:

$$r = C_1 \cdot e^{m_n \Phi^n + \ldots + m_i \Phi^i + \ldots + m_1 \Phi}$$

wherein;

r: Distance (Radius Vector) from the X-ray radiation source to the reflective surface at the angle of inclination $\Phi$, $\Phi$: Angle of inclination, $C_1$: Constant, $m_i$: Constant, and $m_2 \sim m_n$: Constant (at least one of these constants $m_2 \sim m_n$ is a positive constant.)

3. The X-ray analysis apparatus as claimed in claim 1, further comprising a analyzing crystal operable to render the X-ray beam to be monochromatic, said analyzing crystal being disposed on an optical path extending from the X-ray radiation source to the X-ray detector.

4. The X-ray analysis apparatus as claimed in claim 3, wherein said analyzing crystal is disposed on an optical path between the specimen and the X-ray detector.

5. The X-ray analysis apparatus as claimed in claim 3, wherein said analyzing crystal is disposed on an optical path between the X-ray radiation source and the artificial multi-layered grating.

6. The X-ray analysis apparatus as claimed in claim 1, further comprising an X-ray semitransparent mirror disposed on an optical path for allowing a portion of the X-ray beam to undergo a total reflection thereby to reduce a long wavelength component of the X-ray beam while only a short wavelength component of the X-ray beam is allowed to pass therethrough.

7. The X-ray analysis apparatus as claimed in claim 6, wherein said X-ray semitransparent mirror is disposed on an optical path between the X-ray radiation source and the artificial multi-layered grating.

8. The X-ray analysis apparatus as claimed in claim 6, wherein said X-ray semitransparent mirror is disposed on an optical path between the specimen and the X-ray detector.

9. X-ray analysis apparatus comprising:

an x-ray radiation source for generating an x-ray beam;

an analyzing element in the form of an artificial multi-layered grating for diffracting the x-ray beam from the x-ray radiation source to provide a first-order monochromatic diffracted x-ray beam which is converged on a surface of a specimen at a small incident angle sufficient to cause the x-ray beam to undergo a total reflection;

an x-ray detector for detecting a fluorescent x-ray beam emitted from the specimen as said specimen is excited by the first-order monochromatic diffracted x-ray beam and for analyzing the detected fluorescent x-ray beam based on a result of detection by said x-ray detector; and said artificial multi-layered grating having a reflective surface of a predetermined profile and comprising a plurality of lattice planes located on a substrate, said lattice planes having a periodicity respectively increasing in thickness from one end to an opposite end in a direction away from said x-ray radiation source.

10. The X-ray analysis apparatus as claimed in claim 9, wherein said predetermined profile is defined by a system of polar coordinations represented by the following equation:

$$r = C_2 \cdot e^{k_n \Phi^n + \ldots + k_i \Phi^i + \ldots + k_1 \Phi}$$

wherein;

r: Distance (Radius Vector) from the X-ray radiation source to the reflective surface at the angle of inclination $\Phi$, $\Phi$: Angle of inclination, $C_2$: Constant, $k_i$: Constant, and $k_2 \sim k_n$: Constant (at least one of these constants $k_2 \sim k_n$ is a positive constant.)

11. The X-ray analysis apparatus as claimed in claim 9, further comprising an X-ray semitransparent mirror disposed on an optical path for allowing a portion of the X-ray beam to undergo a total reflection thereby to reduce a long wavelength component of the X-ray beam while only a short wavelength component of the X-ray beam component is allowed to pass therethrough.

12. The X-ray analysis apparatus as claimed in claim 11, wherein said X-ray semitransparent mirror is disposed on an optical path between the X-ray radiation source and the artificial multi-layered grating.

13. The X-ray analysis apparatus as claimed in claim 11, wherein said X-ray semitransparent mirror is disposed on an optical path between the artificial multi-layered grating and the specimen.

14. The X-ray analysis apparatus as claimed in claim 9, wherein said incident angle is chosen to be within the range of 0.05 to 0.20 degree.

* * * * *